US008961424B2

(12) United States Patent
Sato et al.

(10) Patent No.: US 8,961,424 B2
(45) Date of Patent: Feb. 24, 2015

(54) ULTRASOUND IMAGE DIAGNOSIS APPARATUS

(75) Inventors: Tomohiro Sato, Tochigi-ken (JP);
Katsuya Hirakui, Tochigi-ken (JP);
Katsuteru Kuramata, Tochigi-ken (JP);
Hideo Onodera, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 556 days.

(21) Appl. No.: 12/778,684

(22) Filed: May 12, 2010

(65) Prior Publication Data
US 2010/0292577 A1 Nov. 18, 2010

(30) Foreign Application Priority Data

May 12, 2009 (JP) ................................. 2009-115872

(51) Int. Cl.
*A61B 8/00* (2006.01)
(52) U.S. Cl.
CPC ................. *A61B 8/00* (2013.01); *A61B 8/4405* (2013.01); *A61B 8/4438* (2013.01)
USPC ............ 600/459; 600/437; 600/439; 600/447
(58) Field of Classification Search
CPC ....... A61B 8/00; A61B 8/4405; A61B 8/4438
USPC ........................... 600/437, 439, 447; 439/364
See application file for complete search history.

(56) References Cited

U.S. PATENT DOCUMENTS

| 5,419,329 | A | * | 5/1995 | Smith et al. | 600/447 |
|---|---|---|---|---|---|
| 5,882,310 | A | * | 3/1999 | Marian, Jr. | 600/459 |
| 6,461,304 | B1 | * | 10/2002 | Tanaka et al. | 600/462 |
| 2002/0146927 | A1 | * | 10/2002 | Uchibori et al. | 439/364 |
| 2008/0064955 | A1 | * | 3/2008 | Miyajima | 600/437 |
| 2009/0171203 | A1 | * | 7/2009 | Avital et al. | 600/439 |
| 2009/0247877 | A1 | * | 10/2009 | Tanaka et al. | 600/462 |
| 2010/0109694 | A1 | * | 5/2010 | Dananay et al. | 324/757 |
| 2010/0292577 | A1 | * | 11/2010 | Sato et al. | 600/459 |
| 2012/0271573 | A1 | * | 10/2012 | Markoff et al. | 702/59 |

FOREIGN PATENT DOCUMENTS

JP        2006-26046        2/2006

* cited by examiner

*Primary Examiner* — Baisakhi Roy
(74) *Attorney, Agent, or Firm* — Oblon, Spivak, McClelland, Maier & Neustadt, L.L.P.

(57) ABSTRACT

An ultrasound image diagnosis apparatus executing lighting-on and lighting-off of a lighting device by detecting an identification (ID) data of a probe or an operation on an operation panel. The ultrasound image diagnosis also includes a lighting device configured to identify a usage state or non-usage state of the ultrasound probe by a lighting color. While an ultrasound examination is performed in a dimly-lit room, a visibility of an ultrasound probe connector can be increased.

16 Claims, 4 Drawing Sheets

ULTRASOUND IMAGE DIAGNOSIS APPARATUS

CROSS-REFERENCE TO RELATED APPLICATIONS

This application claims priority under 35 U.S.C. §119(a) from, and the benefit of, Japanese Patent Application No. 2009-115872, filed on May 12, 2009, the contents of which are expressly incorporated herein by reference in their entirety.

BACKGROUND OF THE INVENTION

A. Field of the Invention

The present invention relates to an ultrasound image diagnosis apparatus, and more particularly to an ultrasound image diagnosis apparatus that can easily perform various operations, such as an exchange of an ultrasound probe, in a darkened room.

B. Background of the Invention

An ultrasound image diagnosis apparatus transmits ultrasound through ultrasound transducers installed in an ultrasound probe to an object, such as a patient, and receives reflected ultrasound (echo signals) due to differences of acoustic impedances of the object's organs so as to display the image of the organ on a monitor. Since an ultrasound image diagnosis apparatus can easily obtain and observe two dimensional images in a real time by simply touching an ultrasound probe to a patient's body surface, it is widely used for diagnosing various functions or status in a patient's body, such as an abdominal organ, a cardiologic organ, and biopsy.

In accordance with the diagnosis purpose, a plurality of ultrasound probes, each having a different frequency and a different surface shape of transducers, can be appropriately used. To appropriately use the different kinds of ultrasound probes, a plurality of connectors are provided on a main body of the ultrasound image diagnosis apparatus for attaching appropriate ultrasound probes through the plurality of connectors. Thus, a plurality of ultrasound probes are detachably connected to the ultrasound image diagnosis apparatus through the connectors. For instance, when three kinds of ultrasound probes are initially connected to the main body of the ultrasound image diagnosis apparatus through three respective connectors, an appropriate ultrasound probe can be selectively used by performing a switching operation on the main body side of the ultrasound image diagnosis apparatus. Such ultrasound probes connected to the main body of the ultrasound image diagnosis apparatus are referred to as active ultrasound probes.

On the other hand, a relatively less frequently used ultrasound probe can be prepared so as to immediately connect to one connector of the main body of the ultrasound image diagnosis apparatus at a necessary time. Such an ultrasound probe is referred to as a standby ultrasound probe. Conventionally, it has been proposed to use the less frequently used standby ultrasound probe by exchanging it with an active ultrasound probe in accordance with a necessity to use that standby ultrasound probe (for instance, see Japanese Patent Application Publication 2006-26046).

When the number of the standby ultrasound probes desired to be used exceeds the number of connectors provided on the ultrasound image diagnosis apparatus, one of the active ultrasound probes connected to one connector needs to be removed and an appropriate ultrasound probe is then attached to that connector by selecting among the standby ultrasound probes. However, since the examination room has a dimmed light during the ultrasound examination so as to easily observe a monitor screen of the ultrasound image diagnosis apparatus, it has been difficult to exchange the ultrasound probes. Thus, it has been difficult for an operator to remove one probe from the connector and put another probe to the connector in a dimly-lit room. Thus, there have been serious drawbacks of visibility and operability. Further, since the major portions of the main body of the ultrasound image diagnosis apparatus except an operation panel are difficult to see easily, for instance, it has been difficult to confirm a printed record of the ultrasound examination in the darkened room.

SUMMARY OF THE INVENTION

The present invention addresses these and other problems and drawbacks and provides an ultrasound image diagnosis apparatus that can easily perform various operations in a darkened room for ultrasound examinations. In particular, an embodiment of the present invention provides an ultrasound image diagnosis apparatus that can control a lighting-on and lighting-off around the probe connector portion by detecting an identification (ID) signal of a connection status of an ultrasound probe. Further, an embodiment of the present invention provides an ultrasound image diagnosis apparatus including display devices provided on a main body side of the diagnosis apparatus for indicating an operation state of ultrasound probes by detecting the ID signal for indicating operation or non-operation of ultrasound probes.

One aspect of an embodiment of the ultrasound image diagnosis apparatus consistent with the present invention is an ultrasound image diagnosis apparatus including a plurality of connectors for detachably connecting to a plurality of ultrasound probes; a lighting unit provided in a vicinity of a respective position of the plurality of connectors; and a control unit configured to control a lighting-on or a lighting-off of the lighting unit in accordance with an operation on an operation panel or attachment or release of an ultrasound probe to and from the plurality of connectors.

According to an embodiment of the present invention, while the ultrasound examination is performed in a dimly-lit room, the visibility in and around the connector unit for coupling the ultrasound probe can be increased. Consequently, it becomes possible to easily exchange ultrasound probes during the examination. Further, a wrong selection of the ultrasound probe among a plurality of probes in a dimly-lit room can be avoided. Since the exchange of the ultrasound probes can be correctly performed in a short time, the efficiency of ultrasound examinations can be improved and the burdens on a patient and the operator can be reduced.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number are used throughout the drawings to describe the same or like parts. In the drawings.

DESCRIPTION OF PREFERRED EMBODIMENTS

Figure 1:
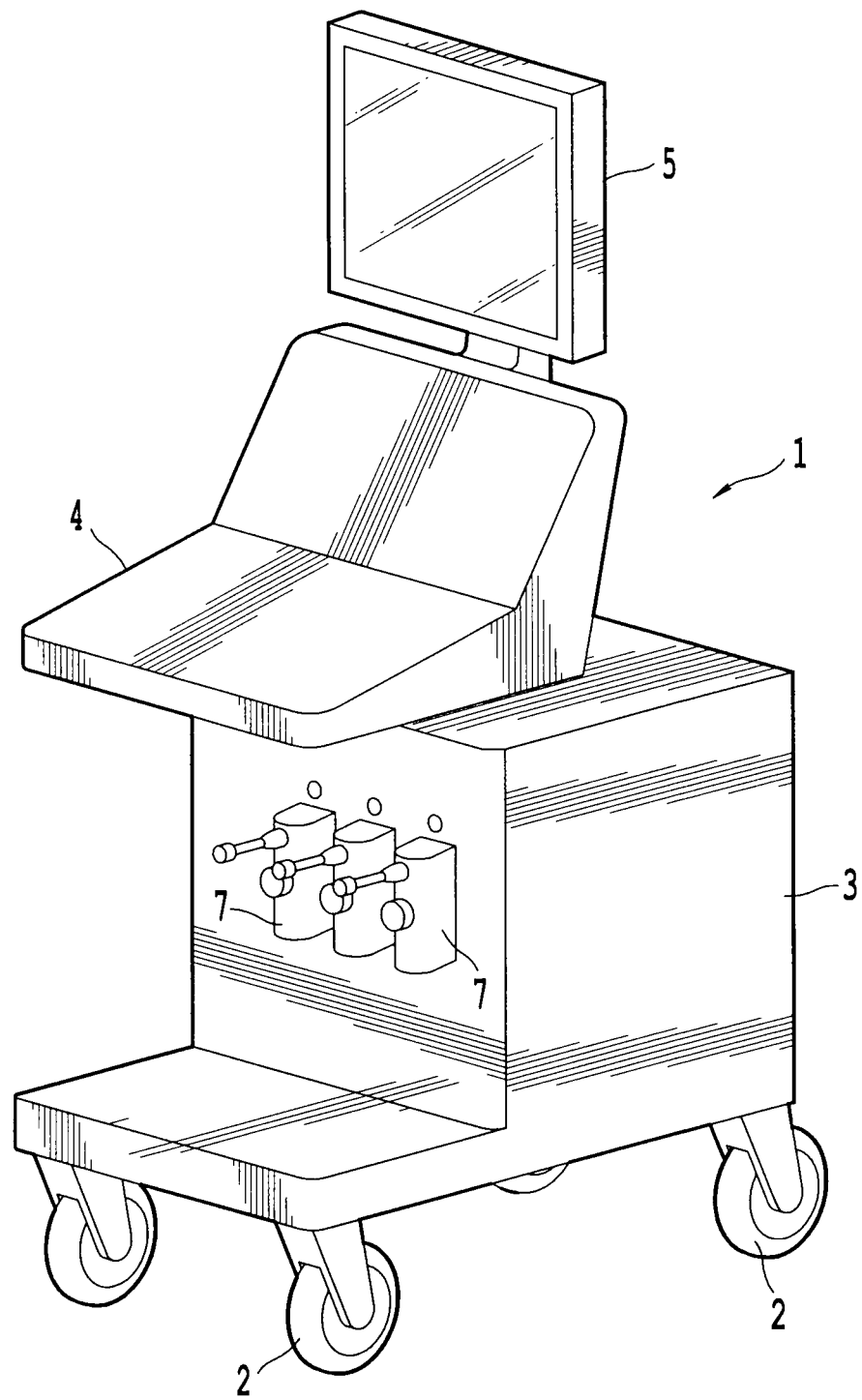
FIG. 1 is an external view of one embodiment of an ultrasound image diagnosis apparatus consistent with the present invention.

FIG. 1 illustrates an ultrasound image diagnosis apparatus 1 consistent with an embodiment of the present invention. The ultrasound image diagnosis apparatus 1 includes a main body 3 of the ultrasound image diagnosis apparatus 1, an operation panel 4, a monitor 5 for displaying ultrasound images, and an ultrasound probe 6 (not shown in FIG. 1, shown in FIG. 3) for performing transmissions and receptions of ultrasounds to and from an object (e.g. a patient). The operation panel 4 includes a touch panel and a keyboard for performing various input operations by an operator. Usually, the operation panel 4 is provided on an upper portion of the main body 3 of the ultrasound image diagnosis apparatus. To easily move the main body 3 of the ultrasound image diagnosis apparatus, it is desirable to attach casters 2 under the main body 3.

On the main body 3 of the ultrasound image diagnosis apparatus, a plurality of connectors 7a, 7b, 7c (which may simply be referred to as element 7 below) are provided to electrically couple to a plurality of ultrasound probes 6. As illustrated in FIG. 1, the plurality of connectors 7 are provided on a front side surface of the main body 3 of the ultrasound image diagnosis apparatus so as to be located at a position under the operation panel 4. In the shown embodiment of FIG. 1, three connectors 7a, 7b, 7c are provided so as to always couple three kinds of ultrasound probes 6 as the active ultrasound probes.

Figure 2:
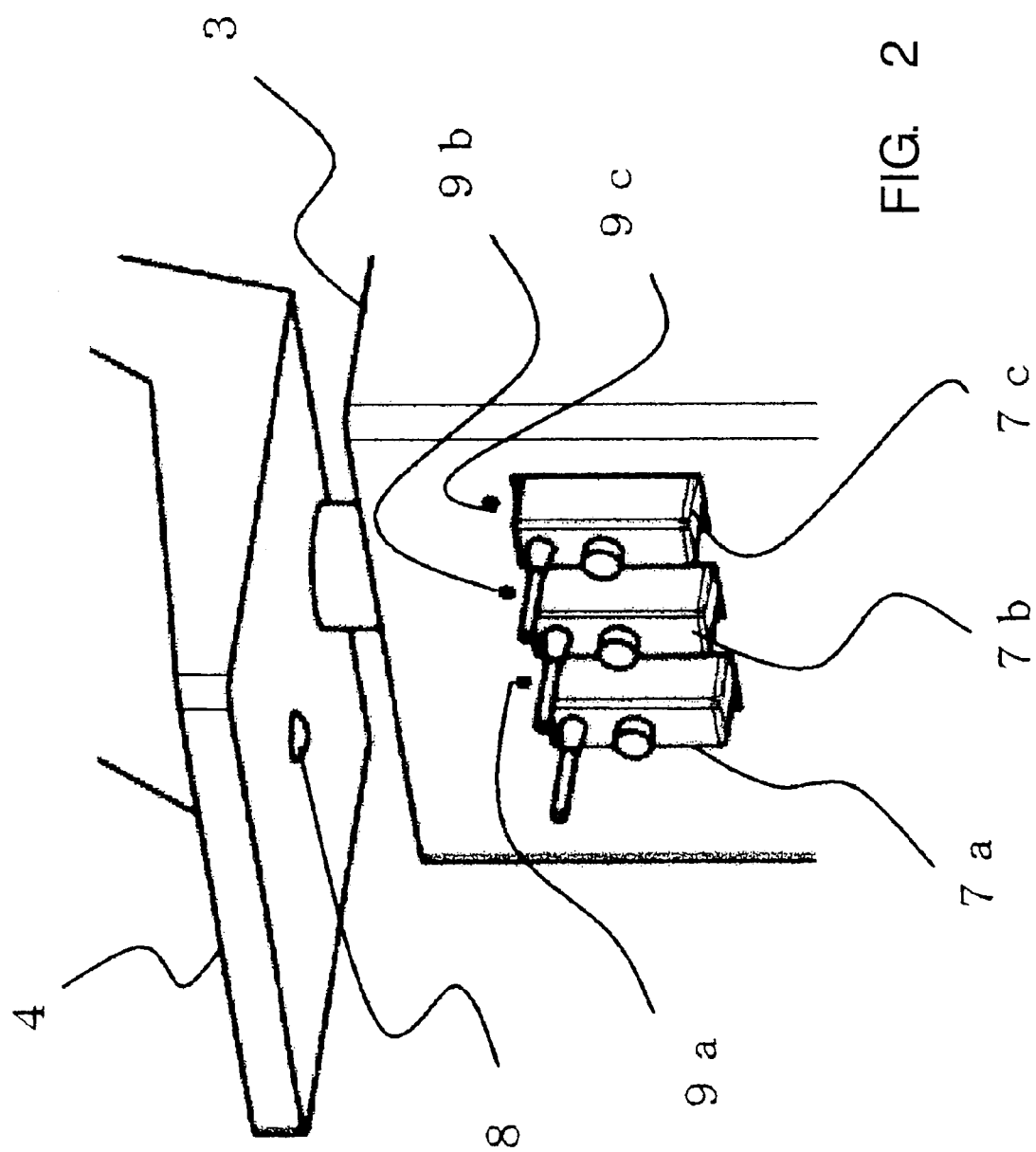
FIG. 2 illustrates the connector unit of the ultrasound image diagnosis apparatus shown in FIG. 1.

As illustrated in FIG. 2, a lighting device 8 is provided under the surface of the operation panel 4 so as to light up the three connector units 7a, 7b, and 7c. Further, three display devices 9a, 9b, and 9c (which may be simply referred to as element 9 below) are respectively provided near the connectors 7a, 7b and 7c. The lighting device 8 and the display devices 9 are, for instance, formed of light emitting diodes.

Figure 3:
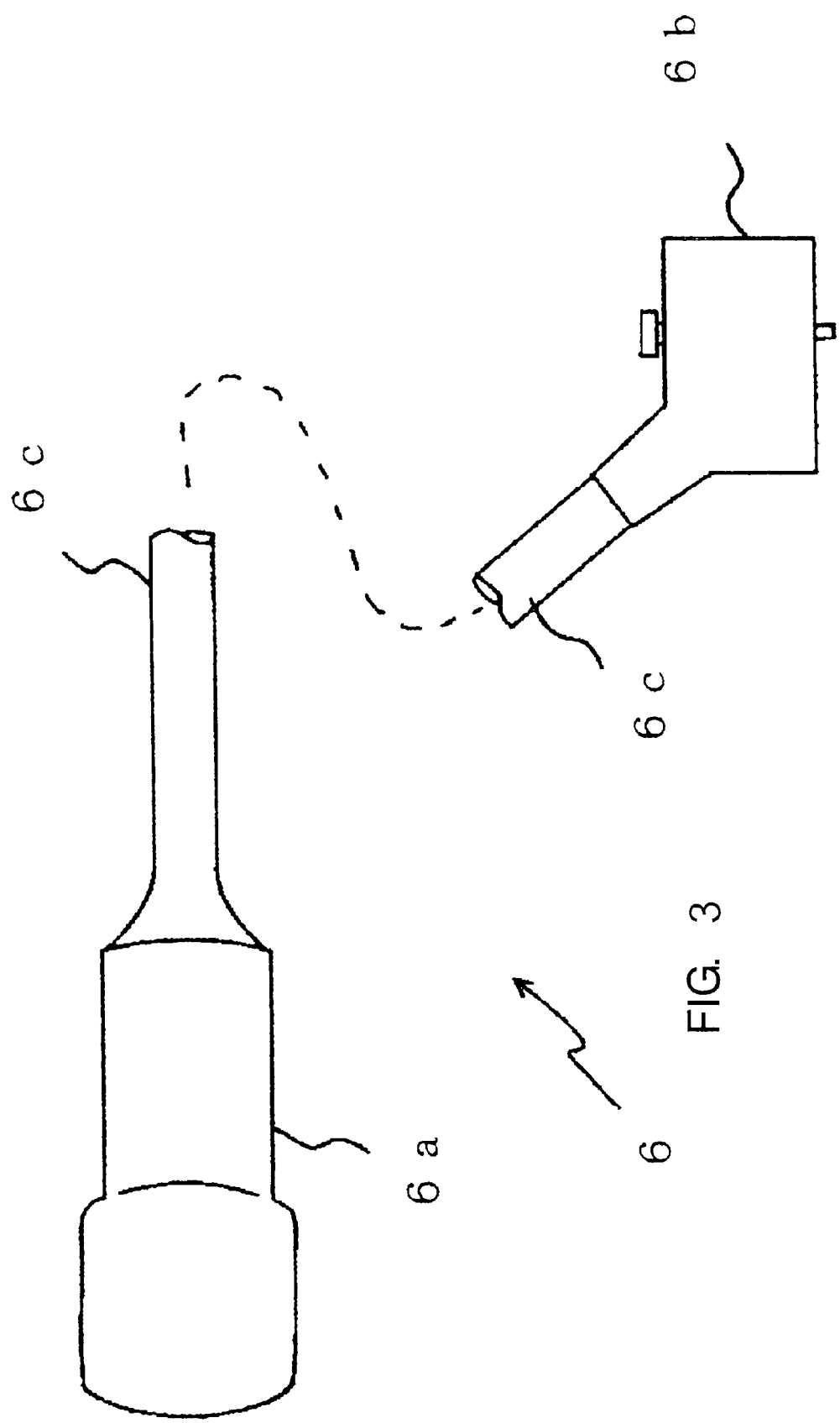
FIG. 3 illustrates one embodiment of an ultrasound probe.

As illustrated in FIG. 3, an ultrasound probe 6 includes an ultrasound probe head 6a including a plurality of transducers for transmitting and receiving ultrasounds, a cable 6c connected to the ultrasound probe head 6a, and a probe connector 6b for coupling the cable 6c to at least one of the connectors 7a, 7b, 7c of the main body 3 of the ultrasound image diagnosis apparatus 1. On the main body 3 of the ultrasound image diagnosis apparatus 1, a holding unit (not shown) for keeping the active ultrasound probes and a hanger unit (not shown) for housing the standby ultrasound probes are also provided.

Figure 4:
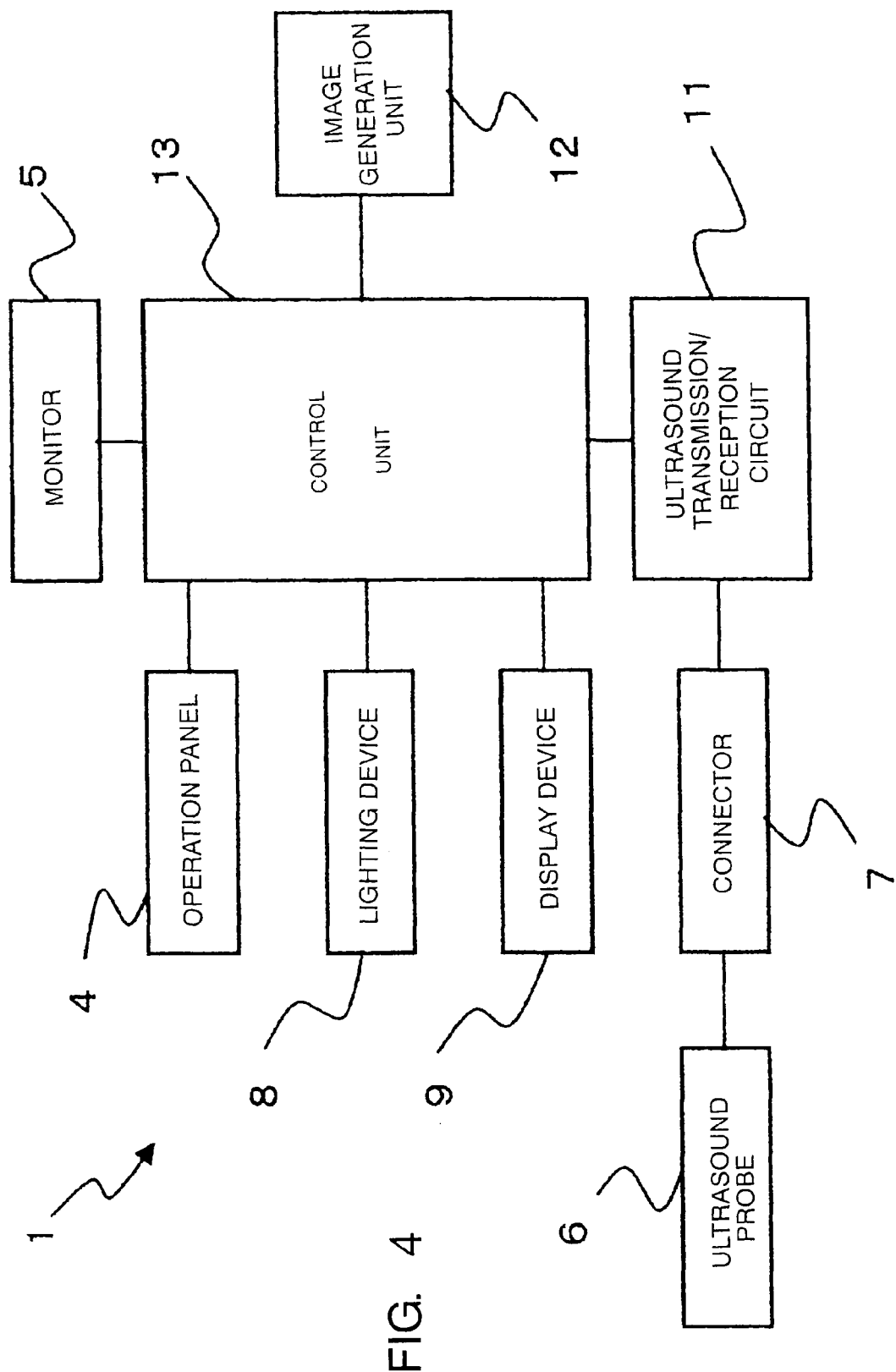
FIG. 4 is a block diagram illustrating another construction of an ultrasound image diagnosis apparatus of one embodiment consistent with the present invention.

Referring to FIG. 4, a block diagram of an ultrasound image diagnosis apparatus such as shown in FIG. 1 and consistent with an embodiment of the present invention will be explained. The ultrasound image diagnosis apparatus 1 includes an ultrasound transmission/reception circuit 11, an image generating unit 12, and a control unit 13 in the main body 3 of the apparatus. The connectors 7 are provided on the main body 3 of the apparatus so as to be located under the operation panel 4 (only one connector 7 is shown in FIG. 4). The connectors 7 are coupled to the control unit 13 through the ultrasound transmission/reception circuit 11. The ultrasound transmission signals generated in the ultrasound transmission/reception circuit 11 are supplied to the ultrasound probe 6 through the connector 7. The ultrasound transmission signals are converted to ultrasound pulses at the ultrasound probe head 6a for transmitting onto an object (e.g. a patient).

The ultrasound probe head 6a receives the echo pulses reflected from the patient based on the transmitted ultrasound pulses and converts the received echo pulses into electric signals for transferring them to the transmission/reception circuit 11 as received signals. The received signals are supplied to the image generating unit 12 for generating ultrasound images by performing a prescribed process under a control of the control unit 13. The ultrasound images are displayed on the monitor 5. The control unit 13 includes a CPU and a memory (both are not shown) and controls the entire operations of the ultrasound image diagnosis apparatus 1 including the operation panel 4, the monitor 5, the lighting device 8, and the display device 9.

Each of the ultrasound probes 6 has a probe ID that represents a type and a model number of the ultrasound probe as an identification data. By coupling the ultrasound probe 6 to the connector 7 provided on the main body 3 of the ultrasound image diagnosis apparatus, the probe ID is identified by a CPU in the control unit 13. Based on an identified result of the ID, an appropriate operation mode for the ultrasound probe 6 is automatically set up. Thus, appropriate operation conditions for the ultrasound transmissions/receptions and image generations for the coupled ultrasound probe 6 are automatically set up. When the ultrasound probe 6 is released from the main body 3 of the ultrasound image diagnosis apparatus, a freezing operation is performed for stopping transmissions/receptions of ultrasounds to avoid damage to the ultrasound transmission/reception circuit 11.

When the ultrasound probe 6 is coupled to the connector 7 on the main body 3 of the ultrasound image diagnosis apparatus, the control unit 13 automatically identifies its probe ID. Thus, the control unit 13 automatically identifies which type of ultrasound probe 6 is coupled to which connector 7. Accordingly, when an operator selects a desired ultrasound probe 6 through the operation panel 4, it becomes possible to generate images and to acquire measured data under an appropriate operation mode for the selected ultrasound probe 6.

When the ultrasound image diagnosis apparatus 1 is used under a condition in which three ultrasound probes 6 are respectively coupled to the three kinds of connectors 7a, 7b, and 7c such as shown in FIG. 2, suppose that an operator is now using a first ultrasound probe coupled to the connector 7a. During an examination being performed, the operator may desire to use another type of ultrasound probe 6 different from the presently coupled ultrasound probe. In such a case, the operator firstly pushes a freeze button or switch on the operation panel 4 for stopping transmission/reception operations of the presently used ultrasound probe 6 and removes the ultrasound probe 6 from the connector 7a.

In one feature possible in the present invention, the selection of such a freeze button or switch on the operation panel 4 can be utilized as a trigger to turn on the lighting device 8 above the connectors 7a, 7b, 7c. Thereby, the visibility of the connectors 7a, 7b, 7c can be improved for a subsequent exchange of ultrasonic probes 6. The operation panel 4 can also include a probe exchange switch that an operator selects when the operator wishes to exchange a probe, and operation of such a probe exchange switch can also serve as the trigger to cause the lighting device 8 to light-up the area around the connectors 7a, 7b, 7c, so that again that portion is well lit for a subsequent exchange of ultrasonic probes 6.

Alternatively, when removing the ultrasound probe 6 from one of the connectors 7, the control unit 13 will then detect that no ID signal is supplied from that connector 7. Based on that detection of no ID signal, the control unit 13 supplies a lighting-on instruction signal to the lighting device 8. By lighting-on the lighting device 8, the portion around the connector 7 is lighted up. Accordingly, the visibility of the connector 7 portion is improved even when the ultrasound examination is executed in a dimly-lit examination room. Thus, it become possible to easily select a newly desired ultrasound probe among the standby ultrasound probes in a housing unit and to easily couple the newly selected ultrasound probe to an appropriate connector 7.

By coupling the newly selected ultrasound probe 6 to an appropriate connector 7, the control unit 13 then automatically identifies the new probe ID. By identifying the new probe ID, the control unit 13 sends a lighting-off signal to the lighting device 8. Of course, it is possible to light off the lighting device 8 by using a timer at a prescribed time interval after sending the lighting-on signal from the control unit 13.

The display devices 9 are provided to easily distinguish a particular ultrasound probe during usage from the other non-usage ultrasound probes among the three kinds of active ultrasound probes 6 respectively coupled to the connectors 7a, 7b, and 7c. To do so, the display devices 9a, 9b, and 9c are respectively provided near the connectors 7a, 7b, and 7c. A probe ID of the ultrasound probe 6 under usage is automatically identified by the control unit 13. The control unit 13 can then transmit a lighting signal to one of the display devices 9a, 9b, 9c corresponding to the respective connector 7a, 7b, 7c coupled to the identified ultrasound probe 6 to light on the display device 9. For instance, suppose that the ultrasound probe 6 coupled to the connector 7a is now in an operation state, the display device 9a is lighted on and the other display devices 9b and 9c are lighted off.

Thereby the lighting-on or the non-lighting of the display devices 9a, 9b, 9c can display the operation status or the non-operation status of the ultrasound probes connected to the respective connectors 7a, 7b, 7c. Further the differences of the operation and non-operation states of the ultrasound probes can be displayed by displaying different colors of the display devices 9a, 9b, 9c. For instance, each display device 9 can be lit by a green color during an operation status, and each display device 9 can be lit by an orange color in the non-operation status.

According to the above-discussed embodiment consistent with the present invention, the visibility in the vicinity of the connector units 7a, 7b, 7c at any time when an exchange of the ultrasound probes 6 is needed during an ultrasound examination can be increased in a dimly lit room. Thus, selecting a desired ultrasound probe 6 among the standby ultrasound probes in a housing unit can be made easier and it is easier to couple the desired ultrasound probe 6 to the correct connector 7a, 7b, 7c. Consequently, since the exchange of the ultrasound probes 6 can be correctly performed in a short time, the efficiency of ultrasound examinations can be improved and the burdens on a patient and the operator can be reduced.

According to the above-described embodiment consistent with the present invention, it also becomes possible to easily identify an ultrasound probe 6 as in a usage state or a non-usage state based on a lighting state of the display devices 9. Thus, it is possible to avoid damages of transmission/reception circuit 11 due to an erroneous release of an ultrasound probe 6 from the connectors 7a, 7b, 7c.

The present invention is not limited to the above-mentioned embodiments. For instance, it is possible to provide a specific switch for lighting-on and lighting-off of the lighting device 8. While in the embodiment the connectors 7 are provided on a front surface of the main body 3 of the ultrasound image diagnosis apparatus so as to be located at a position under the operation panel 4 and under the ultrasound image diagnosis apparatus main body 3, it is possible to provide the lighting device 8 at any other appropriate position for lighting the connectors 7.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

The invention claimed is:

1. An ultrasound image diagnosis apparatus comprising:
   a plurality of connectors for detachably connecting to a plurality of ultrasound probes;
   a lighting unit separated from the plurality of connectors and provided in a vicinity of a respective position of the plurality of connectors to impinge light output from the lighting unit onto the plurality of connectors; and
   a control unit configured to control a lighting-on of the lighting unit in accordance with an operator removing one of the plurality of ultrasound probes from a respective of the plurality of connectors.

2. The ultrasound image diagnosis apparatus according to claim 1, wherein the control for lighting-on of the lighting unit is executed by no longer detecting an identification (ID) signal of the ultrasound probe when the operator removes the one of the plurality of ultrasound probes from the respective of the plurality of connectors.

3. The ultrasound image diagnosis apparatus according to claim 1, wherein the control unit is further configured to control a lighting-on time for the lighting unit.

4. The ultrasound image diagnosis apparatus according to claim 1, further comprising a plurality of display units separate from the lighting unit provided in a vicinity of respective of the plurality of connectors to identify a usage or non-usage state of ultrasound probes connected to the respective plurality of connectors.

5. The ultrasound image diagnosis apparatus according to claim 4, wherein the display units identify the usage or non-usage state of the ultrasound probes by a lighting color.

6. The ultrasound image diagnosis apparatus according to claim 4, wherein the display units identify the usage or non-usage state of the ultrasound probes by different lighting colors of light emitting diodes.

7. An ultrasound image diagnosis apparatus comprising:
   a plurality of connectors for detachably connecting to a plurality of ultrasound probes;
   a lighting unit separated from the plurality of connectors and provided in a vicinity of a respective position of the plurality of connectors to impinge light output from the lighting unit onto the plurality of connectors; and
   a control unit configured to control a lighting-on of the lighting unit in accordance with an operator activating a control on an operation panel to stop operation of a currently used one of the plurality of ultrasound probes.

8. The ultrasound image diagnosis apparatus according to claim 7, further comprising a control unit configured to control a lighting-on time for the lighting unit.

9. The ultrasound image diagnosis apparatus according to claim 7, further comprising a plurality of display units separate from the lighting unit provided in a vicinity of respective of the plurality of connectors to identify usage or non-usage of ultrasound probes connected to the respective plurality of connectors.

10. The ultrasound image diagnosis apparatus according to claim 9, wherein the display units identify the usage or non-usage state of the ultrasound probes by a lighting color.

11. The ultrasound image diagnosis apparatus according to claim 9, wherein the display units identify the usage or non-usage state of the ultrasound probes by different lighting colors of light emitting diodes.

12. An ultrasound image diagnosis apparatus comprising:
- an ultrasound apparatus main body including a plurality of connectors for detachably connecting to a plurality of ultrasound probes;
- an operation panel provided on the main body of the apparatus;
- a lighting unit separated from the plurality of connectors and configured to light up a portion of the main body including the plurality of connectors to impinge light output from the lighting unit onto the plurality of connectors; and
- a control unit configured to control a lighting-on or a lighting-off of the lighting unit in accordance with (1) an operator removing one of the plurality of ultrasound probes from a respective of the plurality of connectors or (2) an operator activating a control on an operation panel to stop operation of a currently used one of the plurality of ultrasound probes.

13. The ultrasound image diagnosis apparatus according to claim 12, wherein the control unit is further configured to control a lighting-on time for the lighting unit.

14. The ultrasound image diagnosis apparatus according to claim 12, further comprising a plurality of display units separate from the lighting unit provided in a vicinity of respective of the plurality of connectors to identify a usage or non-usage state of ultrasound probes connected to the respective plurality of connectors.

15. The ultrasound image diagnosis apparatus according to claim 14, wherein the display units identify the usage or non-usage state of the ultrasound probes by a lighting color.

16. The ultrasound image diagnosis apparatus according to claim 14, wherein the display units identify the usage or non-usage state of the ultrasound probes by different lighting colors of light emitting diodes.

\* \* \* \* \*